United States Patent [19]

Chikama

[11] Patent Number: 5,106,381
[45] Date of Patent: Apr. 21, 1992

[54] BENDING DEVICE FOR AN ENDOSCOPE, CATHETER OR THE LIKE

[75] Inventor: Toshio Chikama, Tokyo, Japan

[73] Assignee: Kabushiki Kaisha Machida Seisakusho, Tokyo, Japan

[21] Appl. No.: 591,671

[22] Filed: Oct. 1, 1990

[30] Foreign Application Priority Data

Oct. 13, 1989 [JP] Japan ............................ 1-119235[U]

[51] Int. Cl.⁵ .................................................. A61M 25/00
[52] U.S. Cl. ...................................... 604/282; 604/95; 604/280; 128/772
[58] Field of Search .................. 128/4, 772; 604/95, 604/270, 280, 282

[56] References Cited

U.S. PATENT DOCUMENTS

| | | | |
|---|---|---|---|
| 4,236,509 | 12/1980 | Takahashi et al. | 128/4 |
| 4,580,551 | 4/1986 | Siegmund et al. | 128/4 |
| 4,659,195 | 4/1987 | D'Amelio et al. | 350/574 |

FOREIGN PATENT DOCUMENTS 1170586  5/1964  Fed. Rep. of Germany ......... 604/95

Primary Examiner—C. Fred Rosenbaum
Assistant Examiner—C. Maglione
Attorney, Agent, or Firm—Fish & Richardson

[57] ABSTRACT

A bending device for use in an endoscope, a catheter or the like is of a simple construction having a frame, a resilient thin plate, and operating wires. The frame has a generally cylindrical shape as a whole, and has annular portions disposed respectively in planes substantially perpendicular to the axis of the frame, the annular portions being juxtaposed in an axial direction of the frame. The resilient thin plate is received in an internal space of the frame. Recesses are formed in each of opposite lateral edges of the resilient thin plate, and are juxtaposed in a longitudinal direction of the resilient thin plate. The annular portions of the frame are engaged respectively in the recesses in each of the opposite lateral edges of the resilient thin plate, so that any adjacent ones of the annular portions are spaced a predetermined distance from each other. The resilient thin plate has slits extending in a direction of the width of the resilient thin plate and spaced from one another in the longitudinal direction of the resilient thin plate, so that the resilient thin plate has a reduced bending resistance.

12 Claims, 2 Drawing Sheets

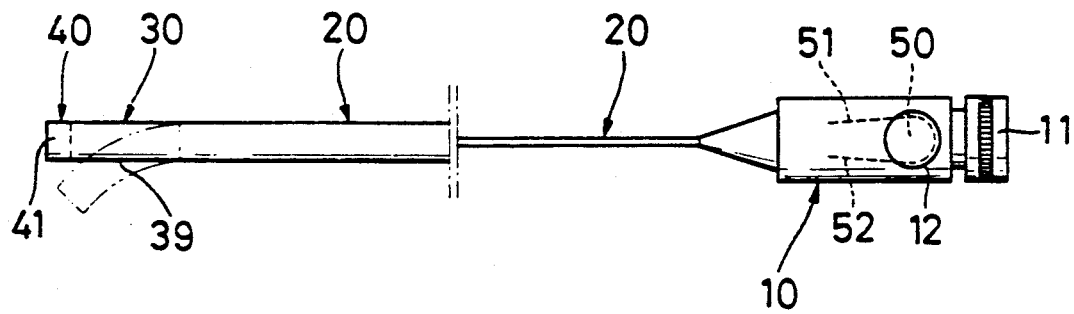
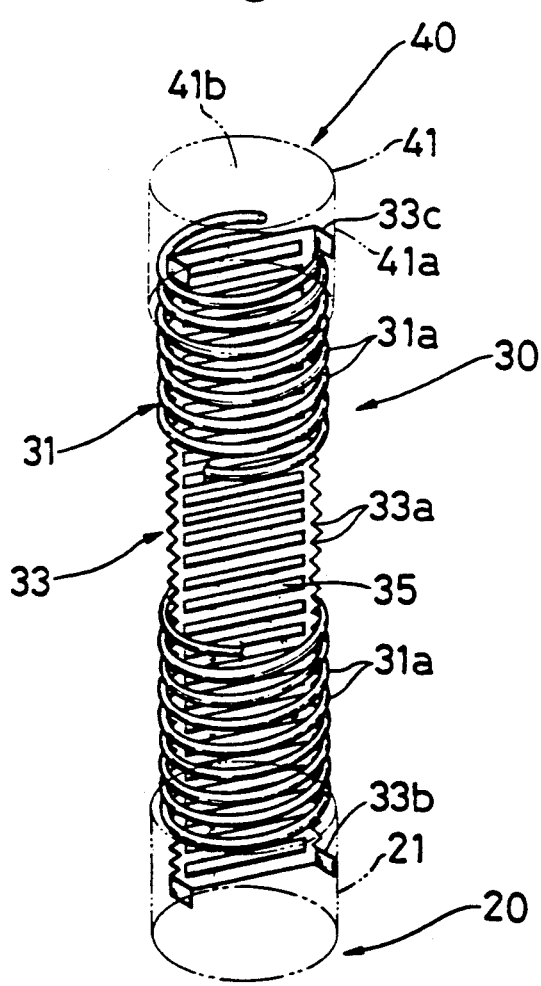
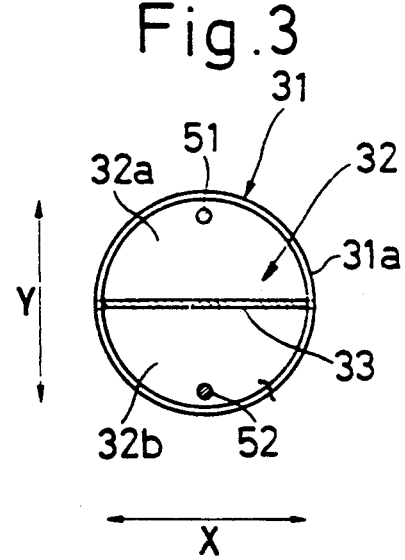
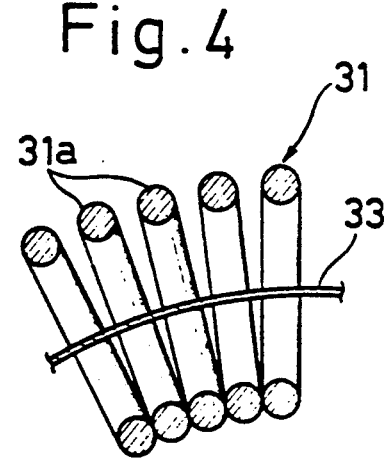

BENDING DEVICE FOR AN ENDOSCOPE, CATHETER OR THE LIKE

BACKGROUND OF THE INVENTION

This invention relates to a bending device for use, for example, in an endoscope.

As is well known, an endoscope comprises a hollow body, a flexible insertion portion extending from a front end of the body, a flexible bending portion extending from a distal end of the insertion portion, and a rigid portion provided at a distal end of the bending portion. An inspection window and an illumination window are formed at the rigid portion.

Japanese Utility Model Publication No. 9274/77 discloses a flexible tube structure for an endoscope which structure has one coil and a resilient thin plate. FIG. 1 of Japanese Laid-Open (Kokai) Utility Model Application No. 10605/80 shows an example in which this flexible tube structure is applied to a bending portion of an endoscope. More specifically, in the bending portion, the resilient thin plate is received in an internal space defined by the coil and extends in the longitudinal direction of the coil. Recesses are formed in each of opposite lateral edges of the resilient thin plate, and are juxtaposed in the longitudinal direction of this plate. The turn portions of the coil are engaged in the recesses. The bending portion is bent in a direction perpendicular to the resilient thin plate by an operating wire, so as to direct an inspection window and an illumination window of the rigid portion toward a desired direction.

The above bending portion is simple in construction, and can be easily manufactured, and particularly, this bending portion can be advantageously applied to the type of endoscope required to have a very narrow bending portion. However, in this bending device, a bending resistance possessed by the resilient thin plate can not be disregarded. For this reason, a reduction of the operating force has been limited. When a narrow operating wire is used to save the internal space, the lifetime of the operating wire is short.

SUMMARY OF THE INVENTION

It is therefore an object of this invention to provide a bending device which can be operated with a small force, and is excellent in durability.

According to the present invention, there is provided a bending device comprising:

(a) a frame having a generally cylindrical shape as a whole and having an internal space therein, the frame having annular portions disposed respectively in planes substantially perpendicular to an axis of the frame, and the annular portions being juxtaposed in an axial direction of the frame;

(b) a resilient thin plate received in the internal space of the frame to divide the internal space into a pair of space portions, recesses being formed in each of opposite lateral edges of the resilient thin plate and juxtaposed in a longitudinal direction of the resilient thin plate, diametrically-opposite sections of each of the annular portions of the frame being engaged respectively in a corresponding pair of the recesses formed respectively in the opposite lateral edges of the resilient thin plate, so that any adjacent ones of the annular portions are spaced a predetermined distance from each other, and the resilient thin plate having a number of holes formed therethrough; and (c) operating wire means for bending the frame and the resilient thin plate, the operating wire means having a proximal end portion adapted to receive an operating force, and the operating wire means having a distal end portion substantially fixed relative to a distal end portion of the frame.

BRIEF DESCRIPTION OF THE DRAWINGS

FIG. 1 is a partly-enlarged, schematic view of an endoscope incorporating a bending device according to the present invention;

FIG. 2 is an enlarged cross-sectional view of an internal structure of the bending portion;

FIG. 3 is a cross-sectional view of the internal structure of the bending portion;

FIG. 4 is a fragmentary view showing the condition of bending of a coil and a resilient thin plate in an exaggerated manner;

DESCRIPTION OF THE PREFERRED EMBODIMENTS OF THE INVENTION

Figure 5:
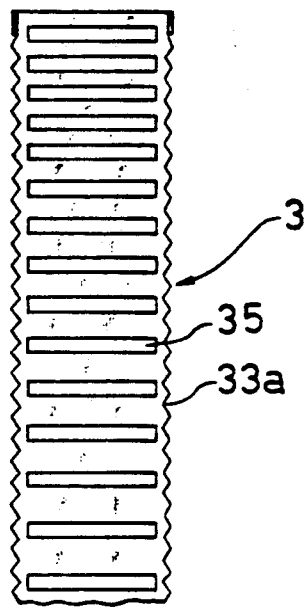
FIGS. 5 to 8 are front-elevational views of portions of modified resilient thin plates, respectively.

A preferred embodiment of the invention will now be described with reference to the drawings.

An endoscope shown in FIG. 1 comprises a hollow body 10, an insertion portion 20 extending from a front end of the body 10, a bending portion (bending device) 30 extending from a distal end of the insertion portion 20, and a rigid portion 40 provided at a distal end of the bending portion 30. Each of the insertion portion 20 and the bending portion 30 has a tubular shape, and is so flexible as to be bent, and is very narrow as compared with that of an ordinary endoscope.

An ocular tube 11 is mounted on the proximal end of the body 10, and a manipulation dial 12 is mounted on the peripheral wall of the body 10. A cable (not shown) is fixedly secured at one end to the peripheral wall of the body 10, and a connector (not shown) to be connected to a light source device is mounted on the other end of this cable.

As shown in FIG. 2, the rigid portion 40 comprises a frame 41. The frame 41 has a cylindrical portion 41a and an end wall 41b formed at a distal end of the cylindrical portion 41a. An inspection window and an illumination window are formed in the end wall 41b. The ocular tube 11 is optically connected to the inspection window via an image transmitting system (not shown) including an optical fiber bundle passing through the body 10, the insertion portion 20 and the bending portion 30. With this arrangement, inspection from the ocular tube 11 can be made. Illumination light from the light source device is applied to the illumination window via an optical fiber bundle passing through the above connector, the above cable, the body 10, the insertion portion 20 and the bending portion 30.

The insertion portion 20 includes a holder coil (not shown) made from a strip or elongated narrow plate. A proximal end of this holder coil is fixedly secured to the body 10, and the distal end of the holder coil is connected to a connecting tube 21. A braid tube (not shown) is fitted on the holder coil, and a tube made of a resin or rubber is fitted on the braid tube.

The construction of the bending portion 30 will now be described in detail with reference to FIGS. 2 and 3. The bending portion 30 includes a coil 31 serving as a frame. The coil 31 has a number of turn portions (annular portions) 31a each having a circular or round shape as viewed in the axial direction of the coil 31 as shown in FIG. 3. Each turn portion 31a is disposed in a plane substantially perpendicular to the axis of the coil 31. The turn portions 31a are juxtaposed in the axial direction of the coil 31. The proximal end of the coil 31 is fixedly secured to the inner surface of the connecting tube 21, and is connected to the distal end of the holder coil of the insertion portion 20 via the connecting tube 21. The distal end of the coil 31 is connected to the inner surface of the cylindrical portion 41a of the frame 41 of the rigid portion 40.

The coil 31 has an internal space 32 extending in the axial direction of the coil 31. A flat resilient thin plate 33 made, for example, of metal or a resin is received within the internal space 32. The resilient thin plate 33 extends in the axial or longitudinal direction of the coil 31 over the entire length of the coil 31. The width of the resilient thin plate 33 is substantially equal to the diameter of the coil 31. For example, the resilient thin plate 33 is disposed perpendicular to the sheet of FIG. 1, and the internal space 32 is divided by the resilient thin plate 33 into a pair of upper and lower space portions 32a and 32b. The above-mentioned optical fiber bundles, etc., are passed through the space portions 32a and 32b.

A pair of pawls 33b are formed on the proximal end of the resilient thin plate 33, and are fixedly secured to the inner surface of the connecting tube 21. Also, a pair of pawls 33c are formed on the distal end of the resilient thin plate 33, and are fixedly secured to the inner surface of the cylindrical portion 41a of the frame 41 of the rigid portion 40.

Each of the opposite lateral edges of the resilient thin plate 33 is serrated or toothed like tooth of a saw, so that a number of triangular recesses 33a are provided in the lateral edge in juxtaposed relation in the longitudinal direction of the resilient thin plate 33. Diametrically-opposite sections of each of the turn portions 31a of the coil 31 are engaged or received respectively in a corresponding pair of mating recesses 33a formed respectively in the opposite lateral edges of the plate 33 and disposed substantially in registry with each other. Almost all of the turn portions 31a of the coil 31 are engaged in the corresponding pairs of mating recesses 33a arranged in the longitudinal direction, so that the coil 31 is supported on the resilient thin plate 33.

Any adjacent turn portions 31a of the coil 31 are engaged respectively in the corresponding adjacent pairs of recesses 33a, so that the adjacent turn portions 31a are kept spaced a predetermined distance from each other.

A plurality of slits 35 are formed through the resilient thin plate 33, and extend in the direction of the width of this plate 33. The slits 35 have an identical rectangular shape, and are spaced from one another at equal intervals in the longitudinal direction of the resilient thin plate 33 over the entire length of the plate 33.

A braid tube, softer than the braid tube of the insertion portion 20, is fitted on the outer periphery of the coil 31, and a tube 39 (only shown in FIG. 1), softer than the tube of the insertion portion 20, is fitted on the outer periphery of this braid tube.

Next, a mechanism for bending the bending portion 30 will now be described. This mechanism includes two operating wires 51 and 52 (not shown in FIG. 2). The operating wires 51 and 52 are fixedly secured to a peripheral surface of a pulley 50 mounted within the body 10, and extend forwardly from the upper and lower portions of the pulley 50, respectively. The pulley 50 is connected to the manipulation dial 12 via a shaft (not shown) extending through the peripheral wall of the body 10.

In the insertion portion 20, the operating wires 51 and 52 are passed respectively through a pair of guide tubes of a small diameter. Each of these guide tubes is formed by spirally winding a wire, and is received within the holder coil. The proximal ends of the guide coils are fixedly secured respectively to diametrically-opposite portions of the body 10 (that is, opposed upper and lower portions of the body 10 in FIG. 1), and the distal ends of the guide coils are fixedly secured respectively to diametrically-opposite upper and lower portions of the inner peripheral surface of the connecting tube 21.

The operating wires 51 and 52 are passed respectively through the space portions 32a and 32b, and are fixedly secured at their distal ends respectively to diametrically-opposite upper and lower portions (FIG. 1) of the cylindrical portion 41a of the frame 41 of the rigid portion 40 by brazing. The positions of fixing of the distal ends of the operating wires 51 and 52, as well as the positions of fixing of the distal ends of the above guide coils, are circumferentially spaced 90° from the opposite lateral edges of the resilient thin plate 33.

In the above construction, since the bending portion 30 has the resilient thin plate 33, the bending portion 30 can not be bent in the direction of the width of the resilient thin plate 33, that is, in a direction X indicated in FIG. 3, and can be bent in a direction perpendicular to the plane of the resilient thin plate 33 (i.e., in a direction Y in FIG. 3 or in an upward-downward direction in FIG. 1).

When the manipulating dial 12 is angularly moved in a counterclockwise direction (FIG. 1), the operating wire 52 is pulled, and the operating wire 51 is loosened. As a result, the bending portion 30 is bent downward in FIG. 1. At this time, since the coil 31 is engaged with the resilient thin plate 33, the pulling force applied by the operating wire 52 will not reduce the length of the coil 31 and hence the overall length of the bending portion 30, thus enabling a proper bending of the bending portion 30. More specifically, as shown in FIG. 4, the distance between those sections of the adjacent turn portions 31a engaged with the resilient thin plate 33 remain unchanged, and the distance between the upper sections of the adjacent turn portions 31a increases whereas the lower sections of the adjacent turn portions decreases. As a result, the bending portion 30 is bent downward.

In contrast, when the manipulating dial 12 is angularly moved in a clockwise direction, the operating wire 51 is pulled, and the operating wire 52 is loosened. As a result, the bending portion 30 is bent upward.

During the bending of the bending portion 30, the turn portions 31a of the coil 31 interfere with one another, thereby maintaining the turn portions 31a in a substantially circular shape, and hence maintaining the cross-section of the bending portion 30 in a substantially circular shape. Also, the interference of the turn portions 31a with one another prevents the bending portion 30 from being bent only at one section thereof, thus ensuring a smooth bending.

During the bending of the bending portion 30, the resilient thin plate 33 is bent in an upward or a downward direction. Since a number of slits 35 are formed through the resilient thin plate 33, this plate 33 offers a small bending resistance. As a result, either of the operating wire 51 and 52 can be pulled with a relatively small force. Also, since the force exerted on the operating wire 51 or 52 can be small, the lifetime of the operating wires 51 and 52 can be increased despite the fact that these operating wires are very narrow or thin.

FIG. 5 shows a modified resilient thin plate 33. The resilient thin plate 33 has slits 35 of an identical shape. The resilient thin plate 33 of FIG. 5 differs from the resilient thin plate 33 of FIG. 2 only in that the intervals between the adjacent slits 35 decrease progressively from the proximal end portion of the plate 33 toward the distal end portion thereof.

Figure 6:
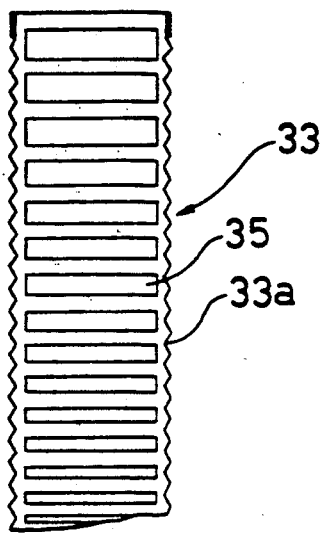

In another modified resilient thin plate 33 shown in FIG. 6, the intervals between adjacent slits 35 are the same over the entire length of the resilient thin plate 33, but the dimensions of the slits 35 in the longitudinal direction of the plate 33, that is, the widths of the slits 35, increase progressively from the proximal end portion of the plate 33 toward the distal end portion thereof.

In each of the resilient thin plates 33 shown in FIGS. 5 and 6, the distal end portion of the plate 33 is smaller in bending rigidity than the proximal end portion thereof. Therefore, the bending portion 30 incorporating the resilient thin plate 33 can be bent more easily at its distal end portion than at its proximal end portion. As a result, the angle between the axis of the inspection window (provided at the rigid portion) and the axis of the insertion portion can be made greater, thus widening the range of inspection. In addition, the rigidity of the proximal end portion of the resilient thin plate 33 is sufficiently high to withstand a compressive force exerted in the direction of the width of the resilient thin plate 33.

Figure 7:
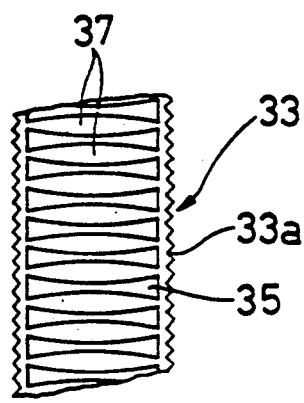

In a further modified resilient thin plate 33 shown in FIG. 7, each slit 35 does not have a rectangular shape, but the width of the slit 35 is smaller at its central portion than at its opposite end portions. In other words, each connecting portion 37, interposed between the adjacent slits 35 and interconnecting the opposite lateral edge portions of the resilient thin plate 33, is wider at its central portion than at its opposite end portions.

The advantages of the resilient thin plate 33 of FIG. 7 will now be described. The coil is held in contact with the opposite lateral edges of the resilient thin plate 33, usually, under a considerable pressure so as to prevent the disengagement of the coil from the recesses 33a. Therefore, the resilient thin plate 33 is subjected to a compressive force in the direction of the width thereof. Since the central portion of the connecting portion 37 is widened, the rigidity of the resilient thin plate 33 in the widthwise direction is greater than that of the resilient thin plate 33 of FIG. 2. Therefore, the resilient thin plate 33 of FIG. 7 is less liable to be flexed upon receiving the above compressive force, thereby maintaining a proper engagement between the coil and the resilient thin plate 33. And besides, the resilient thin plate 33 can be easily bent longitudinally as in the embodiment of FIG. 2.

Figure 8:
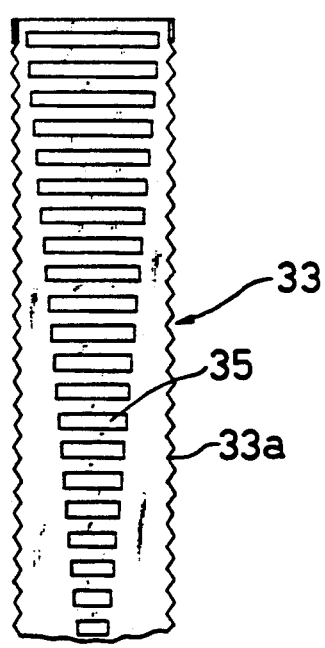

In a further modified resilient thin plate 33 shown in FIG. 8, the lengths of slits 35 (i.e., the dimensions thereof in the direction of the width of the resilient thin plates 33) decrease progressively from the distal end portion of the plate 33 toward the proximal end thereof. The advantages of this construction are almost the same as those achieved by the construction of FIG. 5.

Figure 9:
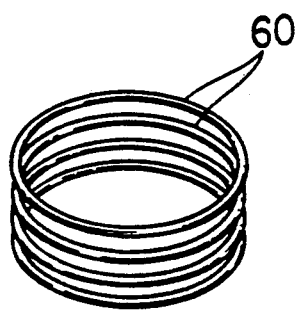
FIG. 9 is a perspective view of a portion of a modified frame of the bending portion.

As shown in FIG. 9, the coil of the bending portion may be replaced by a number of separate rings 60. In this case, the resilient thin plates 33 shown in FIGS. 2 and 5 to 8 can be used. Diametrically-opposite portions of each ring 60 are fitted or engaged respectively in the corresponding pair of mating recesses 33a formed respectively in the opposite lateral edges of the resilient thin plate 33. As a result, the rings 60 are arranged in a row and spaced from one another at equal intervals in the axial direction of the bending portion. The thus arranged rings 60 constitute a frame of the bending portion, and each ring 60 constitutes a respective one of annular portions of the frame. When the resilient thin plate 33 and a number of rings 60 supported thereon are to be inserted into the braid tube during the assembling of the bending portion, an elongated support member is used. This support member has a number of depressions formed in one lateral edge thereof and juxtaposed along the length thereof. That portion of each ring 60 spaced 90° from those portions of the ring 60 engaged with the resilient thin plate 33 is engaged in a corresponding one of the above depressions of the support member. The support member is inserted, together with the resilient thin plate 33 and the rings 60, into the braid tube, and therefore the rings 60 are prevented from swaying during this inserting operation. After the assembling of the bending portion is completed, the support member is removed from the bending portion.

The present invention is not to be restricted to the above embodiments, and various modifications can be made. For example, in the above embodiments, although the slits are provided over substantially the entire length of the resilient thin plate, the slits may be provided only at a portion of this plate, for example, at its distal end portion. The shape of the slits in the resilient thin plate is not limited to those of the above embodiments, and may have any other suitable shape. Instead of the slits, a number of holes of any suitable shape, such as a circular shape, may be formed through the resilient thin plate. The recesses formed in the opposite lateral edges of the resilient thin plate do not need to have a triangular shape, and may have any other suitable shape, such as a rectangular shape and a semi-circular shape.

The use of only one operating wire is possible, in which case the bending portion is bent only in one direction.

The present invention can be applied even if the diameter or thickness of the bending portion is generally the same as that of a bending portion used in an ordinary endoscope.

The bending portion of the present invention can be applied to a medical catheter.

What is claimed is:

1. A bending device comprising:
   (a) a frame having a generally cylindrical shape as a whole and having an internal space therein, said frame having annular portions disposed respectively in planes substantially perpendicular to an axis of said frame, and said annular portions being juxtaposed in an axial direction of said frame;
   (b) a single resilient thin plate received in said internal space of said frame to divide said internal space into a pair of space portions, said resilient thin plate being elongated along the axial direction of said frame, recesses being formed in each of opposite lateral edges of said resilient thin plate and juxtaposed in a longitudinal direction of said resilient thin plate, diametrically-opposite sections of each of said annular portions of said frame being engaged respectively in a corresponding pair of said recesses formed respectively in the opposite lateral edges of said resilient thin plate, so that any adjacent ones of said annular portions are spaced from each other, and said resilient thin plate having a number of holes formed therethrough;

(c) operating wire means for bending said frame and said resilient thin plate, said operating wire means having a proximal end portion adapted to receive an operating force, and said operating wire means having a distal end portion substantially fixed relative to a distal end portion of said frame; and (d) a tube accommodating said frame, said resilient thin plate and said operating wire means, through which tube said operating force is transmitted by said operating wire means to said distal end of said frame to flexibly bend said tube, said frame and said resilient thin plate.

2. A bending device according to claim 1, in which said holes formed through said resilient thin plate are slits extending in a direction of the width of said resilient thin plate and spaced from one another in the longitudinal direction of said resilient thin plate.

3. A bending device according to claim 2, in which said slits are provided at least at a distal end portion of said resilient thin plate.

4. A bending device according to claim 2, in which said slits are provided over substantially an entire length of said resilient thin plate.

5. A bending device according to claim 2, in which said slits have an identical shape, and are spaced from one another at equal intervals in the longitudinal direction of said resilient thin plate.

6. A bending device according to claim 2, in which the distance of the intervals between the adjacent slits increase progressively from a distal end portion of said resilient thin plate toward a proximal end portion of said resilient thin plate.

7. A bending device according to claim 2, in which the widths of said slits in the longitudinal direction of said resilient thin plate decrease progressively from a distal end portion of said resilient thin plate toward a proximal end portion of said resilient thin plate.

8. A bending device according to claim 2, in which the lengths of said slits in a direction of the width of said resilient thin plate decrease progressively from a distal end portion of said resilient thin plate toward a proximal end portion of said resilient thin plate.

9. A bending device according to claim 2, in which the width of each of said slits in the longitudinal direction of said resilient thin plate is narrower at a central portion of said slit than at opposite end portions of said slit.

10. A bending device according to claim 2, in which said operating wire means comprises a pair of operating wires passed respectively through said pair of space portions of said frame.

11. A bending device according to claim 2, in which said frame is constituted by one coil, turn portions of said coil serving as said annular portions of said frame, respectively.

12. A bending device according to claim 2, in which said frame comprises annular rings separate from one another, said rings serving as said annular portions of said frame, respectively.

* * * * *